United States Patent [19]

Bokros et al.

[11] 4,164,045

[45] Aug. 14, 1979

[54] ARTIFICIAL VASCULAR AND PATCH GRAFTS

[75] Inventors: Jack C. Bokros; Hong S. Shim; Axel D. Haubold, all of San Diego, Calif.

[73] Assignee: CarboMedics, Inc., San Diego, Calif.

[21] Appl. No.: 821,602

[22] Filed: Aug. 3, 1977

[51] Int. Cl.² ............................................. A61F 1/00
[52] U.S. Cl. ................................................. 3/1.4; 3/1; 128/334 R; 428/253
[58] Field of Search ................. 3/1, 1.4, 1.5; 128/1 R, 128/334 R, 335; 428/253

[56] References Cited

U.S. PATENT DOCUMENTS

| 3,029,819 | 4/1962 | Starks | 128/334 R |
| 3,304,557 | 2/1967 | Polansky | 128/334 R X |
| 3,526,005 | 9/1970 | Bokros et al. | 3/1 |
| 3,685,059 | 8/1972 | Bokros et al. | 128/1 R X |
| 3,952,334 | 4/1976 | Bokros et al. | 3/1.5 X |

OTHER PUBLICATIONS

Matsumoto et al., "A New Vascular Prosthesis for a Small Caliber Artery", *Surgery*, vol. 74, No. 4, pp. 519–523, Oct. 1973.

*Primary Examiner*—Clifford D. Crowder
*Attorney, Agent, or Firm*—Fitch, Even & Tabin

[57] ABSTRACT

Artificial vascular and patch grafts comprising a flexible elastic fabric substrate of predetermined shape fabricated from small diameter fiber having a tensile modulus of at least about $2\times10^6$ psi, and a thin, smooth, adherent, isotropic carbon coating on the substrate fiber having particular properties including a tensile fracture strain of at least about 5%.

6 Claims, 4 Drawing Figures

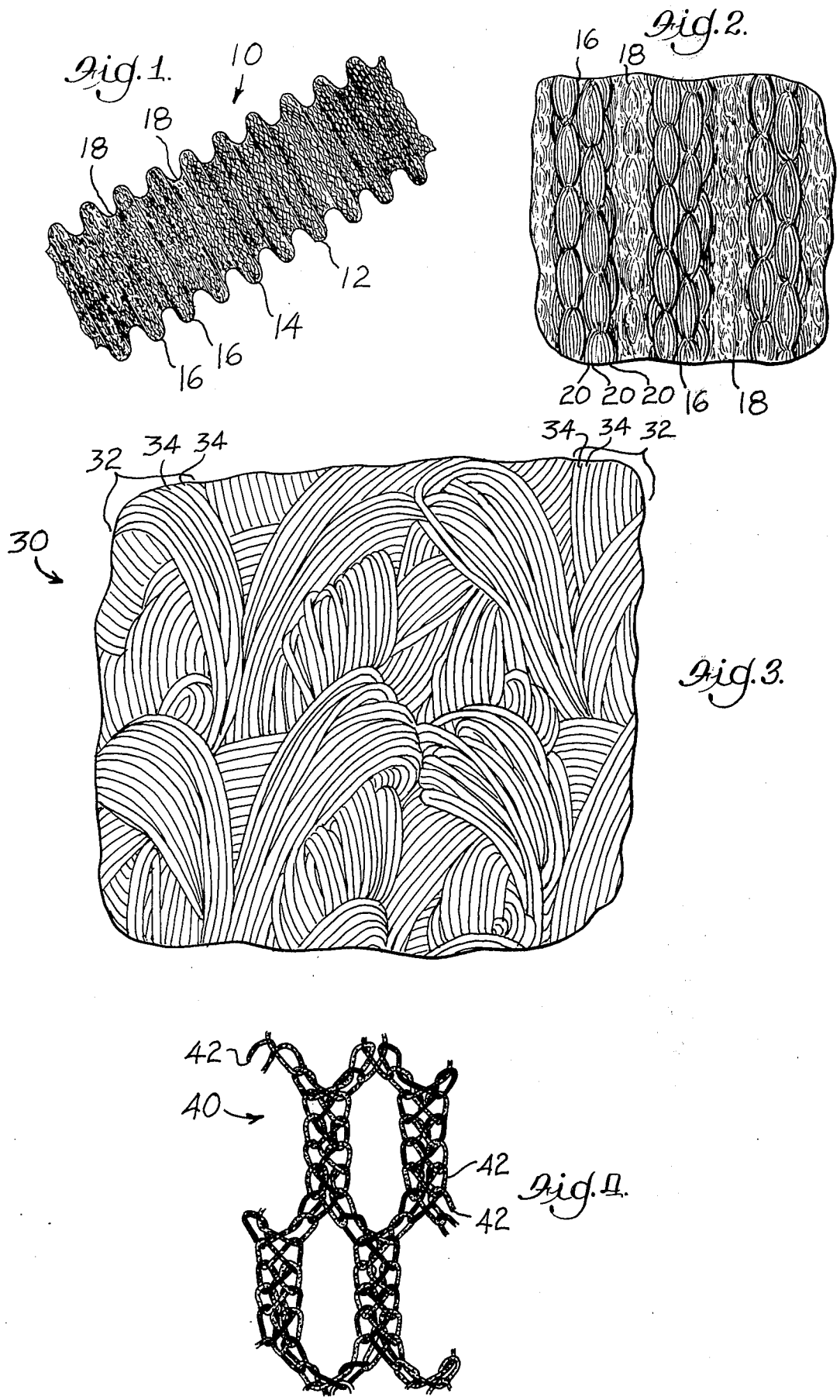

ARTIFICIAL VASCULAR AND PATCH GRAFTS

This present invention relates to flexible fabric grafts for prolonged or permanent implantation in a living body, and, more particularly is directed to flexible fabric grafts such as artificial vascular grafts and artificial patch grafts having a carbon coating. Such materials may also be used to advantage in flexible parts of artificial heart and cardiac assist devices.

The employment of pyrolytic carbon coatings to produce biocompatible and thromboresistant surfaces has produced substantial advancement in the field of medical prosthetic devices, and is described for example, in U.S. Pat. Nos. 3,526,005 issued Sept. 1, 1970 and 3,685,059, issued Aug. 22, 1972. These patents generally describe deposition of pyrolytic carbon coatings, usually from a diluted hydrocarbon atmosphere at atmospheric pressure. Various other techniques have been developed for depositing vapor coatings, for example as by vacuum vapor deposition (VVD) which is also sometimes referred to as vacuum metalizing, physical vapor deposition or evaporative coating, sputtering or as by ion-plating techniques. [e.g., see Marinkovic, et al., Carbon, 14 329 (1976); cited references are incorporated herein by reference]. Coatings deposited by such techniques, which are generally referred to herein as vapor-deposited carbon coatings, have been utilized in prosthetic devices, as described in U.S. Pat. No. 3,952,334. However, despite these advances, there are still deficiencies in the provision of certain prosthetic elements such as artificial vascular and patch grafts.

Conventionally, vascular grafts with diameters greater than six millimeters, fabricated from a variety of synthetic materials, have been used successfully for a number of years in reconstructive surgery. The same degree of success has not been achieved with conventional grafts having diameters smaller than six millimeters. Similarly, while various degrees of success have been realized in respect of synthetic flexible fabrics for patch grafts, there is a need for improved flexible fabrics for reconstructive surgery.

Accordingly, it is an object of the present invention to provide small diameter vascular grafts and materials therefore which are suitable for prolonged or permanent implantation in a living body. It is a further object to provide improved flexible fabrics for reconstructive surgery. These and other objects of the invention will be readily apparent from the following detailed description and the accompanying drawings of which FIG. 1 is a perspective view of one embodiment of an elastic, small-diameter fabric vascular graft in accordance with the present invention;

FIG. 2 is a view of the weft knit structure of the vascular graft of FIG. 1;

FIG. 3 is an illustration of an embodiment of warp knit fabric for reconstructive surgery; and FIG. 4 is an illustration of a mesh knit fabric for reconstructive surgery.

Generally, the present invention is directed to flexible, biologically compatible fabric prostheses suitable for prolonged or permanent implantation in a living body. The fabrics may be provided in tubular form for use as vascular grafts, and are particularly desirable for small diameter grafts.

The flexible fabric prostheses comprise an array of a plurality of carbon-coated, organopolymeric fibers of particular characteristics. The term "fiber array" is meant to include woven and non-woven fabric structures, including knitted and felted structures, with knitted structures being particularly preferred. The organopolymeric fibers are of relatively small diameter which are able to sustain the functional stresses intended for the prosthetic fabric and provide for a desired high degree of flexibility without straining more than about 5 percent. The fibers should generally best have a major diameter dimension of less than about 25 microns, and a minor diameter dimension of at least about 5 microns, although fibers as small as 1 micron might be used in certain applications. By "major diameter dimension" is meant the widest dimension of the fiber in a direction orthogonal to the longitudinal axis of the fiber, and by "minor diameter dimension" is meant the narrowest dimension of the fiber in a direction orthogonal to the longitudinal axis of the fiber. Of course, for a fiber of circular cross section, the major and minor dimensions will be the same, but it should be appreciated that the invention does contemplate fibers of non-circular cross-section. However, deviation from circular fiber cross-sections generally leads to stiffer fabrics because of the increased interfibral friction and increased forces required for bending and unbending of the fiber filaments.

In the prostheses of the present invention, the fibers provide a flexible array in sheet or tubular form so that the prosthesis is provided with a predetermined high degree of flexibility in a prosthetic system which also has beneficial biologically compatible properties of a carbon coating. Furthermore, a high degree of elasticity may be provided through bending of the fibers of the array rather than through substantial tensile elongation of the fibers.

As indicated previously, knit fabric arrays are particularly preferred fiber structures, and in this regard the term "knit" is used generally to include weft knit and warp knit fiber arrays. Weft knit fabric structures (including double-knit structures) utilize interlocked fiber loops in a filling-wise, or weft, direction, while warp knit structures utilize fabric loops interlocked in a length wise, or warp, direction. Weft knit structures generally are more elastic than warp knit structures, but the resiliency of warp knit fabrics is satisfactory to provide a substantial degree of elasticity, or resiliency, to the fabric structure without substantially relying on tensile fiber elongation for such elasticity. Weft knit fabrics generally have two dimensional elasticity (or stretch), while warp knit fabrics generally have unidirectional (width wise) elasticity. The different elasticity properties of the various knit or woven structures may be beneficially adapted to the functional requirement of the particular prosthetic application. In some cases, where little elasticity is desired, the fabric may be woven to minimize in plane elasticity but yet provide flexibility. For large diameter vascular grafts (6 mm diameter or larger) and various reconstructive fabric applications, polyethylene terephthalate fiber fabric arrays of suitably small fiber size may be utilized as preformed substrate materials for subsequent carbon coating. Commercially available woven and knitted fabrics of medical grade Dacron fibers including, single and double velour graft fabrics, stretch Dacron graft fabric and Dacron mesh fabrics, provided the fibers have suitably small diameter and other properties, may be suitable as substrates for application of a suitably thin, high tensile strain carbon coating to provide prostheses in accordance with the present invention. For smaller vascular graft applications (less than 6 mm diameter), and for other applications for which suitable substrates of desired structure are not commercially available, special manufacture will be necessary.

The relatively high degree of flexibility and/or elasticity of the carbon coated fiber arrays of the fabric prostheses is due primarily to the bending of the fibers, rather than substrate fiber elongation which would be incompatible with maintenance of the integrity of a carbon coating on the fibers of the knit structure. The radius of curvature of the individual fibers that will provide a degree of bending without fracture of an adherent carbon coating having a tensile fracture strain of at least 5 percent is determined by the diameter of the fiber. The radius of curvature is approximately $$R = \frac{\text{Diameter of the fiber}}{2 \times \text{allowable strain}}$$

For example, for a diameter of about 10 microns ($=10^{-3}$ cm), the allowable radius R of curvature is:

$$R = \frac{10^{-3}}{2(5 \times 10^{-2})} = 0.01 \text{ cm}$$

Accordingly, the relatively small fiber diameters utilized in the fabric substrate structures provide the prostheses with substantial flexibility without cracking the carbon coating used in the prostheses, which is provided in an isotropic form which can withstand at least about 5% strain without fracture. Smaller fibers are preferred for increased flexibility, and the lower limit of diameter is determined by handling and coating parameters. In order to provide a high degree of flexibility and resiliency (or elasticity), a fiber strand knit is preferred which minimizes localization of individual fiber bending in response to flexure of the fabric. The fiber diameter and modulus are important to assure proper flexure of the fabric so that flexibility is achieved by rearrangement of the fabric structure through bending and unbending of the individual fibers.

Certain physical parameters characterize the substrate fiber of the fabric prostheses, and in this connection, the fibers should be of an organopolymeric material having a tensile strength of at least about 20,000 psi and should be fabricated of medical grade materials. Generally, the fibers will best have a high degree of axial orientation. The modulus is an important parameter, and the organopolymeric fibers should have a tensile modulus of elasticity of about $2 \times 10^6$ psi or more. Polyethylene terephthalate fibers, such as those sold under the trade name Dacron, are particularly preferred because of the biocompatability of such polyester fibers ["Implants in Surgery," D. Williams, et al., W. B. Saunders Company, Ltd., London (1973)], their strength (e.g., 50,000 to 99,000 psi breaking strength) and stiffness (e.g., modulus of elasticity of about $2 \times 10^6$ psi), which may be almost equal to that of the isotropic carbon coating. Such a high modulus, high strength material can support a relatively large load without straining more than 5% (such that the carbon coating would break). Polyethylene terephthalate fibers may be, for example, about three times tougher and five times stiffer than poly(tetrafluoroethylene).

In view of the small diameter of the substrate fibers, it will generally be desirable in most applications of woven and knitted structures to utilize strands of a plurality of fibers in the fiber array. Usually such strands will have at least 5, and preferably at least 10 individual fibers, with the strands being formed into the desired woven or knitted structure.

In cardiovascular fabric grafts, it is of course desirable that the fabric have a controlled degree of porosity. For cardiopulmonary bypass applications, a densely woven fabric structure with very low porosity such as from about 30 to about 125 cc/minute/cm$^2$ may be utilized as a substrate.

For other cardiovascular applications, knit substrate fabrics having, for example, higher porosities in the range of from about 1200 to about 4200 cc/minute/cm$^2$ may be provided with a suitable, high-strain carbon film. The resulting coated cardiovascular prostheses will generally be preclotted in accordance with conventional practice to establish fluid integrity necessary for the cardiovascular use.

In addition to poly(ethylene terephthalate), other suitable high strength, high modulus organopolymeric substrate materials, provided their biocompatability is demonstrated, include various so-called "high temperature polymers" which have generally been developed in the last decade, such as the high modulus and high tensile strength aromatic polyimides and aromatic polyamides. High temperature polymer fibers which may be used herein exhibit thermal stability at temperatures of 300° C. and higher and are generally characterized as high temperature, high molecular weight, aromatic, nitrogen-linked polymers. Such polymers are well known in the polymer art, and examples of such high temperature polymers include ordered aromatic copolyamides, such as the reaction products of phenylenebis (amino-benzamide) and isophthaloyl chloride, all-aromatic polybenzimidazoles, such as poly [2,2' (m-phenylene)-5,5' (6,6' benzimidazole)], polyoxadiazoles, poly (n-phenyl triazoles), polybenzobenzimidazoles, polyimides and poly (amide-imide) resins. Of course, the biocompatability of such materials should be tested, and medical implant grade materials should be used for prosthetic implants. The preferred organopolymeric fibers contemplated for use herein are medical grade polyethylene terephthalates, but various conventional high temperature polymer fibers commercially available, such as fibers sold under the name Kevlar by DuPont, and having a modulus of about $10 \times 10^6$ psi may prove useful.

As previously indicated, the fiber array of the prostheses of the present invention is provided with an adherent isotropic carbon coating of particular properties, and in this connection, carbon, the organic building block of all body matter, has shown outstanding tissue and blood compatability for a variety of prosthetic device applications.

The carbon coatings may be provided by vapor-deposition techniques such as described in the previously referenced U.S. Pat. No. 3,952,334 to produce strongly adherent carbon coatings which provide a particularly desirable biomedical interface between the prosthetic fabric and the implantation site. In cardiovascular prostheses, the carbon coating should be applied to at least the surface which is intended to be in contact with fluid blood. Of course, for tubular cardiovascular prostheses, at least the interior surface of the prosthesis will have the desired carbon coating. In certain circumstances, it may be desirable to coat both surfaces of cardiovascular and patch grafts of the invention.

The individual fibers will typically be about 10 microns in diameter. The smaller the fiber, the smaller the radius of curvature it can sustain without cracking the particular carbon coating, which can sustain at least about 5% elastic strain before fracture, as previously discussed. In view of the small diameter of the fibers used, it is a desirable advantage that the carbon coating may be provided either by coating the individual fibers or yarn strands, or by coating the assembled strand or fiber array. However, it will be appreciated that weaving or knitting of previously coated fibers may generally tend to introduce bending strain, while coating of the finished fabric prosthesis produces a minimum of strain in the composite structure and therefore is particularly preferred.

In any event, the entire exposed surface of the prosthetic fabric is provided with a carbon layer of particular properties and may be applied while using coating technology, such as described in U.S. Pat. No. 3,952,334. Further in this connection, the carbon coating should be at least about 1000Å degrees (0.1 micron) thick, should be adherent, and in order to provide for large fracture strains, should have BAF (Bacon Anistropy Factor) of about 1.3 or less and preferably about 1.2 or less. Generally, a coating thickness of about 1000 to 7000Å degrees and preferably from about 3000 to about 5000Å degrees of intermediate density of carbon (at least about 1.6 gm/cm$^3$) is employed; greater thicknesses tend to crack and flake. Preferably, the vapor-deposited carbon has a density of about 1.8 gm/cm$^3$, and the density should not exceed about 2.0 gm/cm$^3$. Such vapor-deposited carbon exhibits biocompatible properties and also may be provided with excellent adherence to the small polymer fibers of the high modulus organopolymeric fiber fabric. As a result, the coated fibers exhibit excellent properties for use as a prosthetic fabric device and are considered to be fully acceptable for implantation within the human body in flexible and tensile service in a vascular or patch graft such as an artificial septal patch graft or an aneurism patch graft, or the like. Such fabrics may be used for tissue repair, for support in abdominal surgery and for general reconstructive surgery.

Through the design provision of a limited tensile strain in the individual substrate fibers of not more than 5%, under intended conditions of use, the integrity of the carbon coating is preserved for prolonged or permanent implantation service. In this regard, as previously indicated, woven or knit arrays of small oriented polyethylene terephthalate fibers (e.g., medical grade Dacron) having a high stiffness and high strength are preferred. Other polymers such as aromatic polymers like Kevlar (tensile modulus of $10 \times 10^6$ psi) may also be useful in small fiber form. Thus, an artificial vascular or septal prosthesis may be provided which has a high degree of flexibility together with long-term biocompatability and physical integrity.

Having generally described the flexible fabric prostheses of the present invention, the invention will now be more particularly described with respect to the particular embodiments illustrated in the drawings.

Illustrated in FIG. 1 is a side view of a portion of a small diameter vascular graft 10. The small diameter vascular graft 10 comprises a knit fabric tube 12 of a weft-knit dacron fiber substrate which is substantially similar to a conventional dacron vascular prosthesis. The vascular tube walls are constructed with a plurality of regularly spaced pleats 14 of circumferential ridges 16 and valleys 18 to provide for increased elasticity and extensibility along the axis of the prosthetic vascular graft. In the illustrated embodiment, the vascular graft 10 has an internal diameter (to the innermost interior surface of the valleys 18) of 4 mm, and an external diameter of about 7 mm (to the outermost, exterior surface of the ridges 16) in an unstretched condition. In a fully axially stretched condition, the vascular graft has an internal diameter of about 5 mm and an external diameter of about 5.5 mm. The length of the prosthesis 10 will depend on the surgical repair objective, but it will generally be at least about 5 cm to accommodate vascular attachment at the ends of the artificial graft and may be up to 60 cm or more in length. Of course, larger and smaller diameter vascular grafts may be provided.

Turning now to FIG. 2 in which the knit structure of the vascular graft is shown in more detail, it may be seen that the flexible substrate fiber tube is weft-knit in a jersey structure in tubular form from strands of a plurality of individual small diameter fibers 20. The individual fibers 20 are of circular cross-section and are made of axially oriented polyethylene terephthalate. The fibers have a diameter of about 10 microns, a tensile strength of about 40,000 psi and a tensile modulus of about $2 \times 10^6$ psi.

The fibers of the knit fiber array of the vascular graft 10 have an adherent, carbon coating on the interior surface of the graft 10. In order to insure complete coating of the pleats, the graft is coated in an axially stretched condition, but returns to almost its original condition after coating. The coating on the fibers of the vascular graft 10 is isotropic carbon having a BAF of about 1.3 or less and a maximum thickness of about 3000 Angstroms over fibers at the interior surface. Of course, the coating thickness on the fibers decreases toward the exterior surface, which does not have a carbon coating. Upon implantation, the vascular graft 10 is flexible and fatigue resistant and is biologically compatible in the implantation environment. Further, the knit structure of the graft permits tissue ingrowth from the natural vascular tissue, to provide for effective and natural fixation of the prosthesis. The interior surface of the vascular graft has excellent compatability with blood.

Illustrated in FIG. 3 is an embodiment 30 of carbon-coated flexible fabric prosthetic cloth 30 of knit polyethylene terephthalate fiber which is particularly adapted for cardiovascular bypass utilization, for carotid or intracardiac patch grafting, or for abdominal aortic aneurism repair. As may be seen from the drawing, the fabric prosthesis is warp knit from strands 32 of a plurality of small organopolymeric fibers 34 each having a circular cross-section and a diameter of about 5 microns. The fiber strands 32 are knit in a relatively dense warp knit structure which provides substantial strength and fluid impermeability, while retaining substantial flexibility. The knit substrate is coated in a manner such as that of U.S. Pat. No. 3,952,334, and coating is carried out until a thickness of about 3000 Angstroms of carbon is deposited on the individual fibers. The carbon coating is smooth and uniform, and has a density of about 1.8 gm/cm$^3$, a BAF of about 1.2, and a tensile strain at fracture which is greater than 5 percent.

Like the fibers of the embodiment of FIGS. 1 and 2, the substrate fibers of the coated fiber array are individually coated with the carbon coating and are not substantially bonded together. The individual fibers are thus free to bend and glide over each other in the flexure of the prosthesis. The graft has excellent biocompatability and provides for tissue ingrowth at the tissuejoining edges of the fabric graft. The fabric further has excellent compatability with blood.

While the previously described embodiments have illustrated relatively densely knit materials of relatively low porosity, more loosely woven or knit materials may also be used for prosthetic fabric applications. In this connection, an embodiment 40 of carbon coated mesh knit Dacron fabric is shown in magnified view in FIG. 4, which has a relatively open structure useful in reconstructive surgery. The mesh structure is knit from strands 42 of small diameter Dacron fibers. The fiber mesh substrate has substantial elasticity and resiliency in both weft and warp directions and has an adherent, isotropic carbon coating like that of the substrate of FIG. 3.

It will be appreciated that in accordance with the present invention, artificial cardiovascular and patch grafts have been provided which are particularly adapted for prolonged or permanent implantation in a living body, which are biologically inert, and which are capable of substantial flexible motion in service.

Although the invention has been described with regard to certain preferred embodiments, it should be understood that the scope of the invention is defined in the appended claims.

Various of the features of the invention are set forth in the following claims.

What is claimed is:

1. A flexible artificial fabric prosthesis for prolonged or permanent implantation in a living body, comprising a fiber substrate array of organopolymeric fibers having a tensile modulus of elasticity of at least about $2 \times 10^6$ psi, a tensile strength of at least about 20,000 psi and a fiber diameter of less than about 25 microns, said fiber substrate being adapted to sustain the functional stresses encountered by the implanted prosthesis and to provide a desired high degree of prosthesis flexibility without straining more than about 5 percent, and a dense, adherent isotropic carbon coating on the fibers of at least one side of said fiber substrate array having a BAF of about 1.3 or less, a density in the range of from about 1.6 gm/cm$^3$ to about 2.0 gm/cm$^3$, a thickness of less than about 7000 Angstroms, and a tensile fracture strain of at least about 5 percent, said fibers being individually provided with said adherent carbon coating and not substantially bonded together thereby, whereby said coated fibers are free to bend to a bending radius of about 0.025 cm or less and to glide over each other in the flexure of the prosthesis without substantial breaking of said carbon coating.

2. A carbon-coated fabric prosthesis in accordance with claim 1 wherein said fiber substrate array is a knit array of strands of a plurality of said fibers, said strands each being formed of at least 5 of said fibers.

3. A carbon-coated fabric prosthesis in accordance with claim 2 wherein the substrate fibers are formed of axially oriented polyethylene terephthalate.

4. A carbon-coated fabric prosthesis in accordance with claim 2 wherein the fabric array is a tubular vascular graft prosthesis having a pleated structure.

5. A carbon coated fabric prosthesis in accordance with claim 2 wherein said prosthesis is a septal graft prosthesis.

6. A carbon-coated fabric prosthesis in accordance with claim 2 wherein said fibers have a diameter of about 10 microns, wherein said prosthesis is a vascular graft prosthesis having a diameter of less than 6 mm, and wherein said fibers are free to bend to a bending radius of about 0.01 cm in flexure of said prosthesis without substantial breaking of said adherent carbon coating.